(12) United States Patent
Chiou et al.

(10) Patent No.: US 6,616,923 B1
(45) Date of Patent: Sep. 9, 2003

(54) AQUEOUS COMPOSITIONS FOR FACIAL COSMETICS

(75) Inventors: Win L. Chiou, Burr Ridge, IL (US); Linda L. Chiou, Burr Ridge, IL (US)

(73) Assignee: Chiou Consulting, Inc., Burr Ridge, IL (US)

(*) Notice: Subject to any disclaimer, the term of this patent is extended or adjusted under 35 U.S.C. 154(b) by 0 days.

(21) Appl. No.: 10/206,076

(22) Filed: Jul. 26, 2002

(51) Int. Cl.$^7$ .......................... A61K 31/74; A61K 7/48; A61K 47/32
(52) U.S. Cl. .................... 424/78.3; 424/401; 514/772.4
(58) Field of Search ........................... 424/69, 70, 401, 424/78.3; 514/772.4

(56) References Cited

U.S. PATENT DOCUMENTS

| | | |
|---|---|---|
| 4,151,304 A | 4/1979 | Evans |
| 4,829,092 A | 5/1989 | Nelson et al. |
| 5,376,636 A * | 12/1994 | Rutherford et al. ........... 514/12 |
| 5,514,667 A | 5/1996 | Cullis-Hill |
| 5,800,818 A | 9/1998 | Prugnaud et al. |
| 5,952,275 A | 9/1999 | Feferman et al. |
| 5,980,925 A | 11/1999 | Jampani et al. |
| 5,981,499 A | 11/1999 | Hau |
| 6,153,176 A * | 11/2000 | Kaleta et al. ................ 424/60 |

OTHER PUBLICATIONS

"Glycerol", Martindale: The Complete Drug Reference, 32nd edition Pharmaceutical Press, pp. 1585–1586 (1999).
"Glycerol", The Merck Index: An Encyclopedia Of Chemicals, Drugs, and Biologicals 12th edition, pp. 763–764 (1996).
"Neutrogena® Body Moisturizer", Product Label, 2 pgs. (date unknown).
Neutrogena Healthy Skin® Anti–Wrinkle Cream with SPF 15, Product Label and Directions For Use, 1 pg. (date unknown).
Auriol, F. et al., "Effects of Short–time Hydration on Skin Extensibility", Acta Derm. Venereol., vol. 73, No. 5, pp. 344–347 (Oct. 1993).
Block, L.H., "Medicated Topicals: Epidermal And Transdermal Drug Delivery", Remington: The Science and Practice of Pharmacy, 20th edition, Chapter 44, pp. 836–837 (2000).
Guyton, A.C. et al., "Release Of Energy From The Glucose Molecule By The Glycolytic Pathway" and "Use Of Triglycerides For Energy: Formation of Adenosine Triphosphate", Textbook of Medical Physiology, 10th edition, Chapter 67 and 68, pp. 775 and 783 (2000).
Jemec, G.B.E. et al., "Epidermal Hydration and Skin Mechanics: The Relationship between Electrical Capacitance and the Mechanical Properties of Human Skin In vivo", Acta Derm. Venereol., vol. 70, No. 3, pp. 245–247 (1990).
Jermec, G.B.E. et al., "The Effect of Superficial Hydration on the Mechanical Properties of Human Skin in Vivo: Implications for Plastic Surgery", Plastic And Reconstructive Surgery®, vol. 85, No. 1, pp. 100–103 (Jan. 1990).
Olsen, L.O. et al., "The Influence of Water, Glycerin, Paraffin Oil and Ethanol on Skin Mechanics", Acta Derm. Venereol., vol. 73, No. 6, pp. 404–406 (Dec. 1993).
Van Duzee, B.F., "The Influence of Water Content, Chemical Treatment and Temperature on the Rheological Properties of Stratum Corneum", Journal of Investigative Dermatology, vol. 71, No. 2, pp. 140144 (Aug. 1978).
Van Scott, E.J. et al., "Hyperkeratinization, corneocyte cohesion, and alpha hydroxy acids", Journal of the American Academy of Dermatology, vol. 11, No. 5, Part 1, pp. 867–879 (Nov. 1984).

* cited by examiner

Primary Examiner—Joseph K. McKane
Assistant Examiner—Ebenezer Sackey
(74) Attorney, Agent, or Firm—Merchant & Gould P.C.

(57) ABSTRACT

The present invention describes a highly versatile and effective facial composition containing two very simple human endogenous compounds, glycerin or any other nonvolatile, pharmacologically acceptable, slowly absorbed, water-miscible, liquid organic substance and water, which, when applied topically to facial skin in high concentrations, is surprisingly effective for achieving facial skin improvements. The effect of cosmetic improvements lasts up to 18 hours after one single application of the composition. The novel, clear, transparent, unconventional aqueous composition is especially useful for postmenopausal women.

25 Claims, No Drawings

AQUEOUS COMPOSITIONS FOR FACIAL COSMETICS

FIELD OF THE INVENTION

The present invention relates to improving facial skin with an aqueous composition containing one or more nonvolatile, slowly absorbed, water-miscible, liquid organic substances.

BACKGROUND

There are a number of facial skin care products on the market, most of which are in the form of cream, ointment, lotion, gel or emulsion. The majority of these products are not miscible with water and generally contain numerous ingredients (e.g., about 20 to 40 different ingredients). One problem with these complex facial skin care products is that they are relatively difficult to prepare, often requiring special skills and facilities. Additionally, due to their numerous ingredients and methods of preparation, the products are often very expensive.

Current facial skin care products are also relatively unstable in physical shape and form as well as in chemical composition. This instability, which includes thermal instability, may have a drastic effect on the usefulness of a product which has been exposed to variable temperatures (e.g., ranging from about 0° to about 40° C.) during shipping, storage, or use. Additionally, many of the ingredients present in commercial facial skin care products may break down or degrade quickly upon contact with the environment.

Furthermore, most of the ingredients in commercial facial skin care products are foreign to the human body, and may often cause allergic reactions in those who use these products. Those with sensitive skin may find many of the ingredients in commercial facial skin care products harsh and thus, unacceptable for use.

Thus, there exists a need for facial skin care methods and formulations that are hypo-allergenic, natural, inexpensive, easy to prepare, and highly stable, as well as highly effective in producing facial cosmetic benefits or improvements.

SUMMARY OF THE INVENTION

Unlike the complex facial skin care products described above and currently on the market, the present invention provides for a surprisingly simple, clear, transparent, safe, water-miscible, hypo-allergenic, natural, inexpensive, easy to use, easy to prepare, extremely stable, highly efficient and effective composition for improving the facial skin of humans. This unconventional and yet simple approach for facial skin care comprises a method of using an aqueous composition, i.e., composition or mixture containing one or more nonvolatile, slowly absorbed, water-miscible, liquid organic substance(s) and water for achieving facial cosmetic improvements. For example, a single application of the aqueous, facial cosmetic composition of the present invention results in several beneficial cosmetic effects which last for a long period of time, for example, for at least about 4 to 18 hours. The slowly absorbed, nonvolatile, liquid organic substance and water, preferably in the form of a solution, serves as a very simple, inexpensive, highly effective, protective, mechanical barrier or coating on the facial skin surface which prevents or minimizes evaporation of body water from the surface of the facial skin. Additionally, the facial cosmetic composition of the invention is a highly effective moisturizing agent. Since a liquid organic substance of the present invention, for example, glycerin, is a human endogenous substance, its combination with water provides a composition which is practically free of allergic reactions and extremely safe.

One feature of the present invention is the unexpected discovery that water can be used as a highly effective and efficacious anti-wrinkle and/or anti-line agent. In one embodiment, water is continuously and constantly delivered to the facial skin (excluding chapped or burned skin) for an extended period of time (e.g., for about 4 to about 18 hours, preferably for about 8 to about 15 hours) after a single application of a thin layer of a clear, transparent aqueous composition containing water and one or more nonvolatile, slowly absorbed, water miscible, liquid organic substances. The extended effect of the applied water on the facial skin is analogous to the "morning dew" phenomenon (refreshing and re-vitalizing of the withered leaves and flowers) observed on plants or flowers in the early morning following a light rain or foggy night; watering of withering domestic plants or flowers has been repeatedly observed to result in a reappearance of fresh, shiny, dewy, healthy, wrinkle-free smooth leaves or flowers the next day. Therefore, continuous/daily use of the aqueous composition of the present invention serves as a prophylactic treatment to prevent or minimize the formation of wrinkles and/or lines on the facial skin (see Examples II and III). The beneficial cosmetic effects of the present invention is especially useful on post-menopausal women (see Example III).

A particular embodiment of the present invention is a method of using a facial skin care composition containing glycerin and water, at appropriate ratios, such as one to one, to provide effective improvement of the facial skin of humans. For example, the present invention provides methods for treating lines, wrinkles, and dark spots on the skin. Additionally, the methods of the present invention are capable of treating dry skin and signs of aging. The methods of the present invention are also capable of improving the elasticity and appearance of skin.

The present invention provides a method for cosmetically improving facial skin of humans by administering to the facial skin surface an aqueous composition comprising an effective amount of one or more nonvolatile (not evaporating at normal temperatures and pressures with boiling points higher than about 150° C.), pharmacologically acceptable (not irritating to the skin and causing no adverse effects after being administered and/or absorbed through the skin to the circulating blood), slowly absorbed (absorption occurring for about 4 to about 18 hours, preferably from about 8 to about 15 hours), water-miscible (capable of being mixed homogeneously with water at any ratio) liquid organic substances (e.g., liquid substances with organic chemical structures). The present invention performs much more effectively, up to 36-fold better, than conventional, complex and expensive products (see Example I for moist, dewy and shiny effects).

The invention also provides a method for treating wrinkles on facial skin of a human by administering to the facial skin surface an aqueous composition comprising an effective amount of one or more nonvolatile, slowly absorbed, water-miscible liquid organic substances.

The invention also provides a method for treating age spots on facial skin of a human by administering to the facial skin surface an aqueous composition comprising an effective amount of one or more nonvolatile, slowly absorbed, water-miscible liquid organic substances.

The invention also provides a method for treating lines on facial skin of a human by administering to the facial skin surface an aqueous composition comprising an effective amount of one or more nonvolatile, slowly absorbed, water-miscible liquid organic substances.

The invention also provides a method for treating the signs of aging on facial skin of a human by administering to the facial skin surface an aqueous composition comprising an effective amount of one or more nonvolatile, slowly absorbed, water-miscible liquid organic substances.

The invention also provides a method for increasing the elasticity of facial skin of a human by administering to the facial skin surface an aqueous composition comprising an effective amount of one or more nonvolatile, slowly absorbed, water-miscible liquid organic substances.

The invention also provides a method for improving the texture or appearance of facial skin of a human comprising administering to the facial skin surface an aqueous composition of an effective amount of one or more nonvolatile, slowly absorbed, water-miscible liquid organic substances.

The invention further provides a method for promoting shiny, moist facial skin lasting for at least about 4 hours and up to about 18 hours by administering to the facial skin surface of a human an aqueous composition comprising an effective amount of one or more nonvolatile, slowly absorbed, water-miscible liquid organic substances.

The invention also provides a method of providing nutrients (e.g., large amounts of glycerin and water) to the facial skin of a human by administering to the facial skin surface an aqueous composition containing an effective amount of one or more nonvolatile, slowly absorbed, water-miscible liquid organic substances (e.g. glycerin).

Additional ingredients, such as, for example, vitamins, minerals, amino acids, antioxidants and sunscreening agents, known to improve or treat facial skin when administered orally or topically, can also be simply and inexpensively added to the above aqueous composition for further improving the cosmetic effects.

The invention also provides a very simple and unique method for providing prolonged delivery (e.g., delivery of active ingredients to facial skin tissue for from about 4 and up to about 18 hours) (the length/time of prolonged delivery can be tested by the presence of ingredients left on the facial surface by quantitating residual amounts using appropriate analytical methods) of known or discovered ingredients used to improve facial appearance, including, but not limited to, antioxidants, minerals, amino acids and vitamins A, E and C to human facial skin tissue (including stratum corneum and epidermis) by adding the ingredients to an aqueous composition containing one or more water-miscible, nonvolatile, slowly absorbed, liquid organic substances, such as, for example, glycerin, polyethylene glycol 600 or a mixture thereof, and applying the liquid mixture as a thin layer onto the facial skin. Preferably, the aqueous cosmetic composition contains at least about 20% by weight of the nonvolatile, slowly absorbed, liquid organic substance. The delivery of the additional cosmetic ingredients lasts from about 4 hours to about 18 hours after a single application. The method is particularly useful for ingredients that are not rapidly absorbed from the facial skin, for example, compounds requiring many hours for complete or 90% absorption.

The aqueous composition of the present invention may be applied to facial skin as often as appropriate or desired. Preferably, two facial applications a day (one in the morning and one prior to bedtime) ensures practically continuous cosmetic benefits throughout the day and evening.

DETAILED DESCRIPTION OF THE INVENTION

As used herein, the phrase "facial improvements" includes a reduction in the signs of aging including, but not limited to, a reduction in wrinkles, fine lines, and/or age spots. The phrase "facial improvements" also refers to an increase in skin elasticity, softness, smoothness, dewiness, shininess, and/or firmness. "Facial improvements" further refers to moisturizing of facial skin, treatment of wrinkles, fine lines, age spots and/or the signs of aging, but does not include cleaning of facial skin.

As used herein, the phrase "facial cosmetics" refers generally to products used for facial improvement commonly sold in professional cosmetic stores (e.g., Nieman Marcus).

As used herein the term "treat" includes treating, preventing, ameliorating, or inhibiting a skin condition, including age spots, fine lines, wrinkles, signs of aging, or generally resulting in at least one facial improvement, including an increase in skin elasticity, softness, smoothness, dewiness, shininess, firmness, moisture content and fewer lines, wrinkles and/or age spots.

As used herein, the phrase "aqueous composition" refers to aqueous liquid mixtures that are not emulsions, creams, ointments or lotions, and are, preferably, clear, transparent solutions.

As used herein, the phrase "nonvolatile, slowly absorbed, water miscible, liquid organic substance" refers to liquid organic substances with high boiling points, such as 150° C. or higher, that will not evaporate on the surface of facial skin and can be homogeneously mixed with water at any ratio. Such substances include, but are not limited to, glycerin, polyethylene glycol 400, polyethylene glycol 600 and other polyethylene glycols with different mean molecular weights. Preferably, the liquid organic substance is one that is slowly absorbed by the facial skin surface for about 4 hours to about 18 hours, preferably from about 8 to about 15 hours.

As used herein, "slowly absorbed" is qualitatively defined as the water miscible, liquid organic substance being able to physically remain on the facial skin surface for a long period of time. This is determined by the presence of a layer of the aqueous composition remaining on the facial skin. For example, since glycerin will not evaporate at 37° C., its disappearance from the skin surface indicates its absorption through the facial skin. An aqueous composition containing 50% propylene glycol, a nonvolatile, water miscible, liquid organic substance, disappears from the facial surface in less than two hours, while a composition containing 50% glycerin or polyethylene glycol 400 or 600 remains on the facial skin for about 4 hours and up to about 18 hours.

Preferred compositions useful for carrying out the methods of the invention may consist of one or more water-miscible, liquid organic substances and water, including an aqueous composition of glycerin and water.

Due to its very high boiling point (290° C.; The Merck Index, $12^{th}$ edition, S. Budavari et al., Merck & Co., Inc., Whitehouse Station, N.J. (1996)), glycerin from an aqueous glycerin and water composition applied as a thin layer to the facial skin will not evaporate; instead, it will be very slowly absorbed into the skin over a period of from about 4 hours to about 18 hours (see Example I). Since applied glycerin can be substantially absorbed, although slowly, into the percutaneous tissue, a substantial amount of water can be simultaneously absorbed by the facial skin (through passive diffusion of the hydrated glycerin (water attached to the glycerin molecule). Additionally, the high concentration of water in an aqueous glycerin can be absorbed into the facial skin through a concentration-gradient-driven diffusion process. Furthermore, a high concentration of glycerin on the surface of the facial skin will form a protective, mechanical layer to prevent or minimize loss of body water due to evaporation from the facial skin for a long period time as above described. The absorbed water and the prevention of water evaporation plays a very important role in maintaining the integrity and normal function of the facial skin.

Additionally, glycerin can effectively retain water from an aqueous glycerin solution applied on the facial skin surface. Thus, an aqueous cosmetic product containing glycerin and/or another water-miscible, slowly absorbed liquid organic substance and water applied to the facial skin surface can serve as a powerful, constant moisturizing vehicle and thereby make the facial skin instantly, as well as for many hours (see above) shiny and dewy (see Example I). These results are in sharp contrast with conventional commercial facial cosmetic products where the effects of the product last only about 0.5 to about 2 hours (see Example I; the difference is up to about 36-fold). In one embodiment of the present invention, the applied water serves as a highly effective anti-wrinkle and/or anti-line agent.

Additionally, since glycerin can be metabolized into glucose, glycerol-3-phosphate, pyruvic acid, water and carbon dioxide with the release of energy (Medical Physiology, (2000)), the large amount of glycerin used in one embodiment of the present invention can serve as a nutrient and an energy source for maintenance and improvement of facial skin cells for many hours, as above described, by providing the aforementioned metabolic products.

An appropriate combination of the two active ingredients, a water-miscible, slowly absorbed, liquid organic substance, such as glycerin, and water, can be used for application to the facial skin for moisturization and for treatment of dry facial skin (facial skin with reduced moisture as compared to normal facial skin), lines and wrinkles (a line or crease in the facial skin, such as those caused by sun exposure or old age) and for treatment of dark spots or age spots (facial skin disorder seen with aging or sun exposure) where there are flat patches of increased pigmentation on the facial skin.

Additionally, the above two active ingredients can be administered to the facial skin to reduce the signs of aging (gradual changes in the structure, function and appearance of facial skin, such as drier facial skin, wrinkles and age spots, that occur with the passage of time and do not result from disease, accident or wound). They can also be used in a method for increasing the elasticity of facial skin (the facial skin's ability to stretch) and improving the texture (smoothness or firmness) and appearance (plump, shiny, whiter, dewy, smooth and fresh) of facial skin.

Also, the glycerin and/or another water-miscible liquid organic substance that have been absorbed by the facial skin can function as moisturizing agents underneath the facial skin surface and improve the texture and appearance or quality of the facial skin.

The aqueous composition of the present invention can contain various amounts of water-miscible liquid organic substance(s) and water. For example, a mixture of glycerin and water, both being endogenous substances in humans, can range from about 10% to about 95% by volume glycerin, and preferably about 45% to about 55% by volume glycerin. In another embodiment, the glycerin and water composition may be in the range of about 50% glycerin and about 50% water by volume. Although less desirable, pure glycerin or other water-miscible, slowly absorbed liquid organic substances (e.g., liquids that can absorb water from the air) can also be used alone for achieving similar cosmetic benefits.

Any agents that improve or treat facial skin when ingested orally or applied topically may also be easily and inexpensively added to the aqueous composition above described. These agents may include, for example, nutrients such as vitamin A, E or C, minerals, amino acids, anti-oxidants, sunscreen agents, or one or more skin peeling compounds (e.g., alpha-hydroxyisobutyric acid). Additionally, one or more preservatives (e.g., isobutylparaben) or fragrances may also be added to the aqueous composition. Such agents are preferably hypo-allergenic. A viscosity-enhancing agent, such as carboxymethylcellulose or a derivative thereof or polyacrylic acid polymer in a concentration of about 0.1% to about 2% by weight may also be added to the aqueous composition.

The aqueous composition can be directly applied to the facial skin by any appropriate method, such as a spray bottle, a droplet bottle, a moisturized cotton ball or pad. Although the aqueous composition is primarily useful for facial application, the composition may also be applied to any other part of the human body where skin improvement benefits are desired.

The present method differs from commercially available facial cosmetic and facial skin-care products. First, in most commercially available facial skin-care products, glycerin or other water-miscible organic liquid substances are only present as very minor components in the products and the presence and function of water is not emphasized. For example, the lack of recognition of the great importance of glycerin and water in facial cosmetics is clearly illustrated on the label of a cream product marketed by Neutrogena Corporation (Los Angeles, Calif.). The label of Neutrogena's 26-ingredient Anti-Wrinkle Cream with SPF 15 lists glycerin and water as inactive ingredients. Additionally, many widely used facial cosmetic and facial skin-care products, such as ointments, creams, gels and lotions, typically contain some 15 to 30 exogenous, foreign (not endogenous or natural) to the human body ingredients. When applied to the facial skin surface, water in these commercial products often evaporates very rapidly and a "dry film" is left on the surface. This is in sharp contrast with the clear, transparent, aqueous compositions of the present invention. Surprisingly, after just one application of a 50% aqueous glycerin composition (50% AGS) or a 50% aqueous polyethylene glycol 400 composition (50% APS) to the facial skin, the facial skin feels moist for many hours. Thus, the moisturizing efficiency and effectiveness on the surface, as well as inside, of the facial skin are a dramatic improvement in the appearance of the facial skin (up to 36 fold better) over the currently available commercial products (see Example I). Use of the aqueous facial composition twice daily can virtually produce facial improvements and/or benefits for the entire day.

The aqueous glycerin composition of the invention is much easier to prepare, for example, by merely a one-step mixing of the liquid organic substance and water. The resulting composition is more stable (both chemically and physically stable) over a wide range of temperatures than commercially available creams, ointments, emulsions, gels and lotions. Thus, in addition to the advantageous cosmetic benefits provided by the methods of the invention, the use of an aqueous composition of the present invention provides advantages in cost, ease of preparation, and ease of product handling and storage compared to commercial creams, ointments, emulsions, gels, and lotions.

The present invention will now be illustrated by the following non-limiting examples.

EXAMPLE I

Facial Cosmetic Effects Observed After a Single Application of Aqueous Glycerin Composition (AGS), Aqueous Polyethylene Glycol 400 Composition (APS) or Commercial Facial Cosmetics A 50% (by volume) aqueous glycerin composition (50% AGS; e.g., 100 ml glycerin mixed with 100 ml distilled water) was prepared. This composition was applied in the morning as a thin layer on the left-side of the face of two human subjects. A commercial cream, Elizabeth Arden—Ceramide Time Complex Moisture Cream that contains 37 ingredients with a retail price of $46 for a 48-gram bottle, was applied to the right-side of the face of the same two subjects. Both sides of the face immediately appeared shiny, moist and dewy. However, the right-side of the face lost the shiny, moist and dewy appearance in both subjects within about two hours after application of the cream. The left-side of the face maintained its shiny, moist and dewy appearance for about 12 to 18 hours in both subjects. These results clearly demonstrate that a simple 50% AGS is much more effective (almost 10 fold) in producing a shiny, moist and dewy appearance than the much more expensive commercial cosmetic cream. The above superiority of the 50% AGS was demonstrated repeatedly. No adverse effects were reported.

The performance of the 50% AGS was also similarly compared in two human subjects with another commercial facial cosmetic cream, Loreal Plenitude—Turning Point (Loreal Retail Division of Costar Inc., New York). Loreal Plenitude—Turning Point contains 20 different ingredients. When compared, the shiny, moist and dewy appearance of the subjects facial skin lasted for about 15 hours after one application of the 50% AGS, while Loreal Plenitude—Turning Point lasted only about one hour. Short acting effects, lasting for only about 30 minutes were also demonstrated with other commercial facial cosmetic products including lotions. Therefore, the difference in the length of time for the above cosmetic effect is up to about 36-fold between 50% AGS and commercial cosmetic products.

A 50% (by volume) Aqueous Polyethylene Glycol 400 Composition (50% APS) was also similarly prepared. This composition was applied in the morning to two human subjects. Effects similar to those observed with the above 50% AGS were observed. No adverse effects were reported.

EXAMPLE II

Facial Cosmetic Effects after Two Months of Application of the 50% Aqueous Glycerin Composition (50% AGS)

The 50% AGS was applied twice daily (once in the morning and once before bedtime) for about two months to the right-side face of two human adults, one male and one female. The right side and left side of the subject's faces were compared. In the male subject, the right side was determined to be more tender, shiny, fuller, and firmer. Additionally, the lines beneath the right eye were also found to be smaller, shallower and lighter. Similarly, the right side of the face of the female subject was determined to be more shiny, more tender, "whiter", and practically free of dark spots as compared with the left side of the face of the female subject. The above discovery clearly demonstrated the high effectiveness of the simple 50% AGS in achieving desirable facial cosmetic improvements.

EXAMPLE III

Surprising Facial Cosmetic Results after Five Years of Application of the 50% Aqueous Glycerin Composition (50% AGS) to a Post-menopausal Woman A female subject used various brand-name facial cosmetic products (creams and lotions) twice daily for about three decades. At age 55 and at the beginning of menopause, she started to use 50% AGS twice daily (once in the morning and once prior to bedtime). At age 60, both sides of her face were determined to look younger and much whiter, more shiny, more elastic and firmer than about five to eight years ago. The above results clearly demonstrated the very dramatic effect of such a simple glycerin and water composition in improvement of facial skin appearance and on reversing the signs of aging after long-term application to a post-menopause woman. The test subject did not receive any replacement hormone therapy during the entire study. The present study may be particularly significant because dryness of skin and the related effects are known to occur in woman after menopause.

It is to be understood that the above descriptions are intended to be illustrative, and not restrictive. For example, when necessary, other water-miscible high boiling-point liquids like propylene glycol, polyethylene glycol 400 and polyethylene glycol 600 may also be included in the glycerin and water formulation. Many other equivalents will be apparent to those of skill in the art upon reading and understanding the above description. Additionally, one skilled in the art will be able to ascertain, with no more than routine experimentation, many equivalents to the specific embodiments described herein. These equivalents are intended to be encompassed by the following claims.

What is claimed is:

1. A method for ameliorating facial wrinkles comprising administering to facial skin of a human an aqueous composition, that is not a water-immiscible cream, ointment or lotion, consisting essentially of an effective amount of one or more nonvolatile, slowly absorbed, water-miscible, liquid organic substances selected from glycerin, polyethylene glycol 400, polyethylene glycol 600 and mixtures thereof, and water, wherein the liquid organic substance is present from about 20% to about 55% by volume, and wherein the liquid organic substance is slowly absorbed into the facial skin over a period of time for at least about 4 hours.

2. The method of claim 1, wherein the liquid organic substance is slowly absorbed into the facial skin over a period of time from about 8 hours to about 15 hours.

3. The method of claim 1, wherein the liquid organic substance is present from about 45% to about 55% by volume.

4. The method of claim 1, wherein the aqueous composition consists essentially of glycerin and water.

5. The method of claim 1, wherein the aqueous composition further comprises a viscosity-enhancing agent at a concentration of about 0.1% to about 2% by weight.

6. A method for ameliorating facial lines on skin comprising administering to facial skin of a human an aqueous composition, that is not a water-immiscible cream, ointment or lotion, consisting essentially of an effective amount of one or more nonvolatile, slowly absorbed, water-miscible liquid organic substances selected from glycerin, polyethylene glycol 400, polyethylene glycol 600 and mixtures thereof, and water, wherein the liquid organic substance is present about 20% to about 55% by volume, and wherein the liquid organic substance is slowly absorbed into the facial skin over a period of time for at least about 4 hours.

7. The method of claim 6, wherein the liquid organic substance is slowly absorbed into the facial skin over a period of time from about 8 hours to about 15 hours.

8. The method of claim 6, wherein the liquid organic substance is present from about 45% to about 55% by volume.

9. The method of claim 6, wherein the aqueous composition consists essentially of glycerin and water.

10. The method of claim 6, wherein the aqueous composition further comprises a viscosity-enhancing agent at a concentration of about 0.1% to about 2% by weight.

11. A method for ameliorating dark spots on facial skin comprising administering to facial skin of a human an aqueous composition, that is not a water-immiscible cream, ointment or lotion, consisting essentially of an effective amount of one or more nonvolatile, slowly absorbed, water-miscible, liquid organic substances selected from glycerin, polyethylene glycol 400, polyethylene glycol 600 and mixtures thereof, and water, wherein the liquid organic substance is present about 20% to about 55% by volume, and wherein the liquid organic substance is slowly absorbed into the facial skin over a period of time for at least about 4 hours.

12. The method of claim 11, wherein the liquid organic substance is slowly absorbed into the facial skin over a period of time from about 8 hours to about 15 hours.

13. The method of claim 11, wherein the liquid organic substance is present from about 45% to about 55% by volume.

14. The method of claim 11, wherein the aqueous composition consists essentially of glycerin and water.

15. The method of claim 11, wherein the aqueous composition further comprises a viscosity-enhancing agent at a concentration of about 0.1% to about 2% by weight.

16. A method for increasing the elasticity and firmness of facial skin comprising administering to the facial skin of a human an aqueous composition, that is not a water-immiscible cream, ointment or lotion, consisting essentially of an effective amount of one or more nonvolatile, slowly absorbed, water-miscible, liquid organic substances selected from glycerin, polyethylene glycol 400, polyethylene glycol 600 and mixtures thereof, and water, wherein the liquid organic substance is present about 20% to about 55% by volume, and wherein the liquid organic substance is slowly absorbed into the facial skin over a period of time for at least about 4 hours.

17. The method of claim 16, wherein the liquid organic substance is slowly absorbed into the facial skin surface over a period of time from about 8 hours to about 15 hours.

18. The method of claim 16, wherein the liquid organic substance is present from about 45% to about 55% by volume.

19. The method of claim 16, wherein the aqueous composition consists essentially of glycerin and water.

20. The method of claim 16, wherein the aqueous composition further comprises a viscosity-enhancing agent at a concentration of about 0.1% to about 2% by weight.

21. A method for promoting shiny and moist facial skin surface comprising administering to the facial skin of a human an aqueous composition, that is not a water-immiscible cream, ointment or lotion, consisting essentially of an effective amount of one or more nonvolatile, slowly absorbed, water miscible liquid organic substances selected from glycerin, polyethylene glycol 400, polyethylene glycol 600 and mixtures thereof, and water, wherein the liquid organic substance is present about 20% to about 55% by volume, wherein the liquid organic substance is slowly absorbed into the facial skin over a period of time for at least about 4 hours.

22. The method of claim 21, wherein the liquid organic substance is slowly absorbed into the facial skin over a period of time from about 8 hours to about 15 hours.

23. The method of claim 21, wherein the liquid organic substance is present from about 45% to about 55% by volume.

24. The method of claim 21, wherein the aqueous composition consists essentially of glycerin and water.

25. The method of claim 21, wherein the aqueous composition further comprises a viscosity-enhancing agent at a concentration of about 0.1% to about 2% by weight.

* * * * *